US006814577B2

United States Patent
Blacklock

(10) Patent No.: US 6,814,577 B2
(45) Date of Patent: Nov. 9, 2004

(54) DENTAL PROSTHESIS ABUTMENT AND WAXING SLEEVE ASSEMBLY

(76) Inventor: Gordon D. Blacklock, 14116 Grant Ave., NE., Albuquerque, NM (US) 87123

( * ) Notice: Subject to any disclaimer, the term of this patent is extended or adjusted under 35 U.S.C. 154(b) by 161 days.

(21) Appl. No.: 10/266,693

(22) Filed: Oct. 9, 2002

(65) Prior Publication Data

US 2004/0072127 A1 Apr. 15, 2004

(51) Int. Cl.7 .............................................. A61C 11/00
(52) U.S. Cl. ........................ 433/213; 433/173; 433/174
(58) Field of Search ................................ 433/172, 173, 433/174, 175, 176, 177

(56) References Cited

U.S. PATENT DOCUMENTS

| | | |
|---|---|---|
| 5,073,110 A | 12/1991 | Barbone |
| 5,316,477 A | 5/1994 | Calderon |
| 5,350,301 A | 9/1994 | De Buck |
| 5,350,302 A | 9/1994 | Marlin |
| 5,716,215 A | 2/1998 | Blacklock |
| 5,762,500 A * | 6/1998 | Lazarof ...................... 433/213 |

* cited by examiner

Primary Examiner—John J. Wilson
Assistant Examiner—Candice C. Melson
(74) Attorney, Agent, or Firm—Siemens Patent Services, LC

(57) ABSTRACT

A novel dental prosthesis abutment and waxing core assembly, in which the abutment has an exterior axis which differs from its longitudinal axis, and the waxing sleeve has both interior and exterior axes which differ from one another and from the exterior axis of the abutment, is disclosed. In the present invention the abutment and waxing sleeve assembly cooperates with a conventional anchor having a socket for receiving the abutment, and also adjusts to correct for angular misalignment of the prosthesis. The divergent axes allow for alignment of the prosthesis within the mouth while requiring less modification of the waxing sleeve by removal of material and/or addition of material to the waxing sleeve and abutment, thereby reducing the labor required in producing the prosthesis using prior art waxing sleeves and abutments.

17 Claims, 5 Drawing Sheets

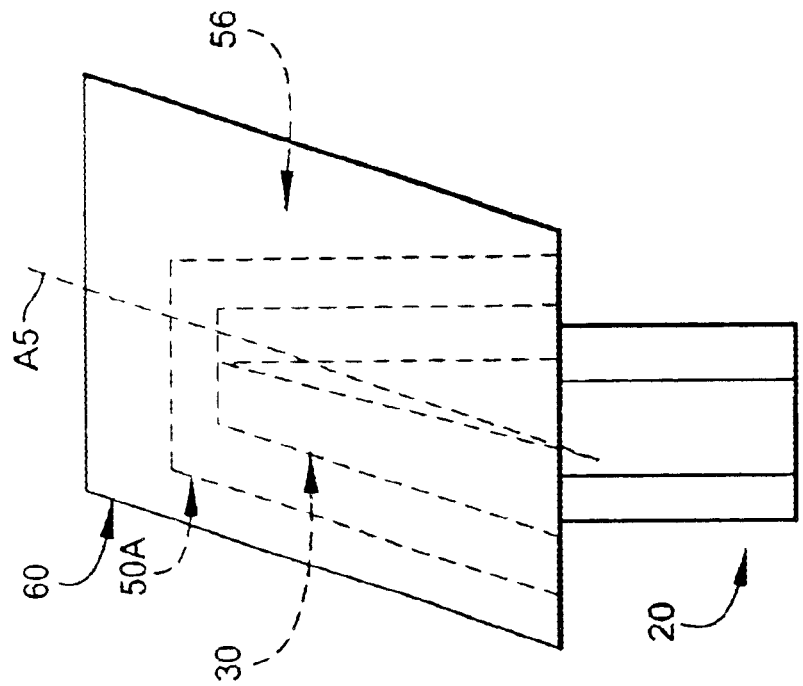
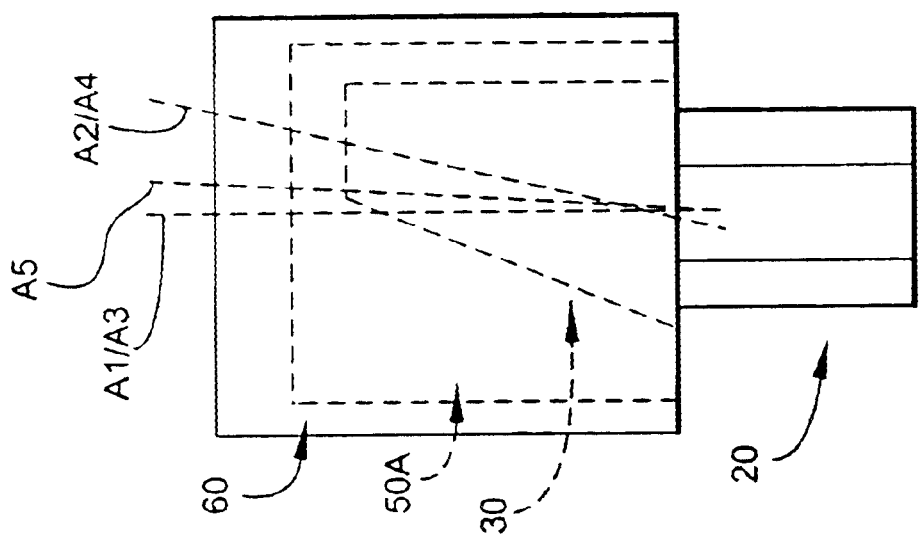

DENTAL PROSTHESIS ABUTMENT AND WAXING SLEEVE ASSEMBLY

This application is related to U.S. Pat. No. 5,716,215, issued to Gordon D. Blacklock on Feb. 10, 1998, included herein by reference.

BACKGROUND OF THE INVENTION

1. Field of the Invention

The present invention relates to an abutment and waxing sleeve assembly for dental implants. More particularly, the abutment and waxing sleeve assembly is constructed such that the abutment is at an angle relative to the exterior of the waxing sleeve, such that a wide variety of angles between the anchor and the abutment may be achieved by rotating the abutment relative to the anchor and trimming the waxing sleeve. Additionally, this type of waxing sleeve, preferably of a lightweight material, having a low melting point, suitable for casting (hereinafter referred to as polymer or polymeric), simplifies the forming of a coping (substructure beneath the enamel) for the prosthesis.

In the dental arts, "post and core" typically refer to a single element, while "abutment" refers to a core which may be formed separately from the post or screw. Hereinafter the term core and abutment will be used interchangeably.

2. Description of the Prior Art

When a dental prosthesis is to be attached to a patient's jaw it must be properly aligned with the other teeth or prostheses so as to be parallel thereto. A problem arises when an anchor receiving the abutment is inserted into the jaw at an angle not suitable for proper alignment. This may occur because bone tissue capable of securely supporting the anchor is not advantageously situated for appropriate placement of the anchor, or because it is simply too difficult to install properly in the available space.

U.S. Pat. No. 5,716,215, issued to the instant inventor on Feb. 10, 1998, discloses a MACHINABLE POST AND CORE having a core which has a first side parallel to the axis of the post and a second side which is oblique to the axis. Excess material of the core may be machined away to produce a post at a desired angle relative to the post. By contrast, the present invention provides an abutment which is fabricated at an angle relative to the waxing sleeve which aids in the formation of a coping for the prosthesis which will cooperate with the abutment.

In U.S. Pat. No. 5,316,477, issued to Luis O. Calderon on May 31, 1994, UNIVERSAL IMPLANT ABUTMENT is disclosed. Calderon's post and core requires considerable grinding of the core to properly align the prosthesis. By contrast, the waxing sleeve of the present invention allows modification of a soft plastic to align the prosthesis.

An IMPLANT COLLAR AND POST SYSTEM is disclosed in U.S. Pat. No. 5,350,302, issued to Gerald M. Martin on Sep. 27, 1994. Some of the components of the post and core assembly have screw bores and mounting cavities which are misaligned, so that the component can be screwed to a supporting component. A subsequently mounted member continues at an angle relative to the supporting component. The various components allow for progressive adjustment to suit conditions as successive components are assembled and oriented at new angles relative to their predecessors. The present invention provides a much simpler apparatus which further incorporates a waxing sleeve which aids in the formation of a coping for the prosthesis which will cooperate with the abutment.

Vincent De Buck discloses a METHOD AND APPARATUS FOR APPLYING A DIRECTION ADJUSTING EXTENSION PIECE IN A DENTAL IMPLANT in U.S. Pat. No. 5,350,301, issued on Sep. 27, 1994. The post and core are provided as two separate, subsequently united structures in this invention. By contrast with the present invention, no part is deflectable into the desired position in the De Buck invention. Rather, in the De Buck device, an assembly incorporating a desired angle must be built up from individual components. The present invention further incorporates the waxing sleeve to aid in the formation of a coping for the prosthesis which will cooperate with the abutment.

None of the above inventions and patents, taken either singly or in combination, is seen to describe the instant invention as claimed.

SUMMARY OF THE INVENTION

The present invention provides an abutment and waxing sleeve assembly which both cooperates with a conventional anchor having a socket for receiving the abutment, and also adjusts to correct for angular misalignment of the prosthesis.

The abutment is formed of a biocompatible material that is chemically stable within the environment of the mouth, such as, but not limited to, titanium. After implantation of the anchor, the abutment is attached, either by a screw through the abutment or a post and core assembly, with rough alignment for the prosthesis being achieved by rotating the abutment relative to the anchor such that the abutment is as close to alignment for the prosthesis as possible. The waxing sleeve is then fit over the abutment. Adjustment grinding is then done on the waxing sleeve, as opposed to on the abutment, as in prior art, thereby speeding the modeling procedure. It is important to note that waxing sleeves available today have the same central axis as the abutment they cover. They are concentric around the central axis of the abutment. This greatly reduces their ease of use.

The novel abutment and waxing sleeve assembly is compatible with conventional anchors, and therefore, does not require fabrication of special anchors.

Accordingly, it is a principal object of the invention to provide an abutment and waxing sleeve assembly which may be variably aligned to allow the associated prosthesis to be correctly aligned with adjacent teeth or prostheses.

It is another object of the invention to provide an abutment and waxing sleeve assembly which may be used with a conventional prosthetic anchor.

It is a further object of the invention to provide an abutment and waxing sleeve assembly which is relatively easy to fabricate and install.

Still another object of the invention is to provide an abutment and waxing sleeve assembly which is economical to use in that the waxing sleeve has an exterior which is not concentric with the core that it cooperates with, thereby requiring less grinding of the abutment, and more versatility Yet another object of the invention is to provide a abutment and waxing sleeve assembly which easily corrects angular deviation of implant to the desired angle through differing angles of deviation of the abutment and the waxing sleeve.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein:

FIG. 9 is a view of a coping for a prosthetic tooth cemented on an abutment with ceramic resembling the patient's tooth coloration on the exterior of the coping.

FIG. 10 is a view of a second coping for a prosthetic tooth formed from a modified waxing sleeve with ceramic resembling the patient's tooth coloration on the exterior of the coping.

DETAILED DESCRIPTION OF THE PREFERRED EMBODIMENTS

Figure 2:
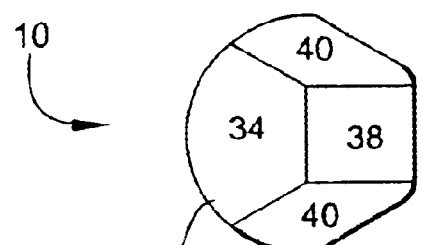
FIG. 2 is a top view of the abutment of the post and core embodiment of FIG. 1.
Figure 1:
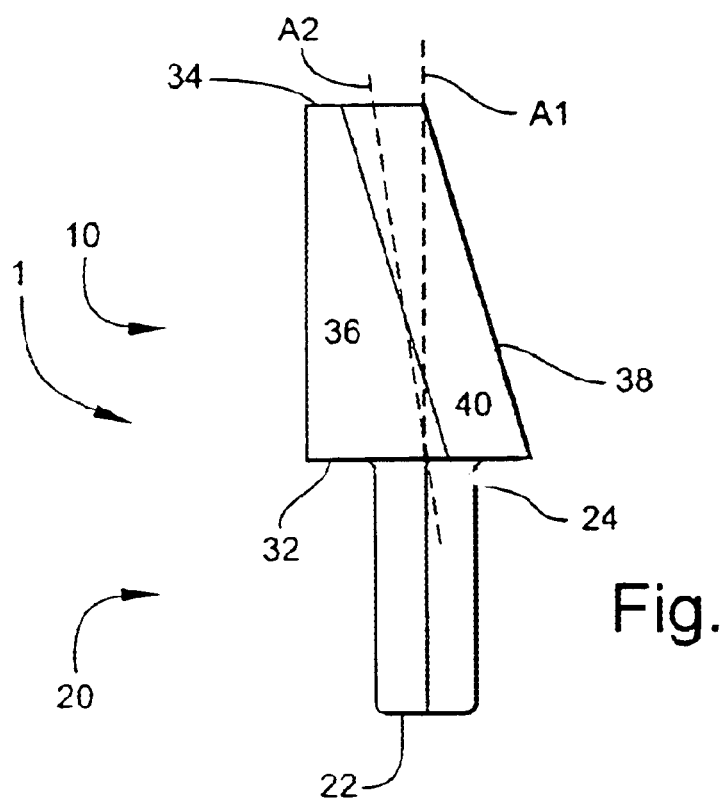
FIG. 1 is a side view of the abutment of the present invention in a post and core embodiment.
Figure 3:
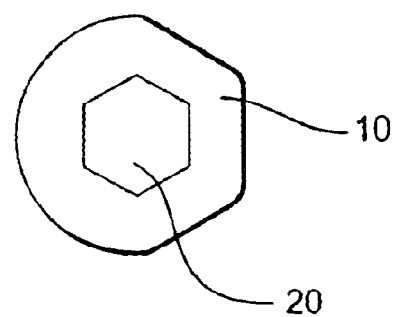
FIG. 3 is a bottom view of the post and core of the embodiment of FIG. 1

Referring first to FIGS. 1 thru 3, the novel abutment 10 of the present invention is presented in a post and core assembly embodiment 1. A post 20 is adapted for internally mating with a standard dental implant anchor (not shown), and abutment 10 is adapted for internally mating with a coping 50A of dental prosthesis 60, (FIGS. 9 and 10).

Post and core 1 is typically formed, as either a single element (as depicted) or separate, joinable, elements, of a biocompatible material such as, but not necessarily limited to, titanium, gold, or a silver-palladium alloy, as are commonly used in dental practice. It would be evident to one skilled in the art that other materials could be used with equal effectiveness, so long as the material used is permanent and stable in an oral environment (i.e., does not degrade and is not toxic when placed in the mouth).

Post 20 has an axial length, with an insertion end 22, adapted for mating with the cavity (not shown) of an anchor (not shown) previously imbedded within a patient's jaw, and a post juncture end 24. Post 20 is typically hexagonal in cross section, although it would be evident to one skilled in the art that any shape compatible with the shape of the cavity within an anchor would be equally suitable without departing from the spirit of the present invention.

In this case, abutment 10 is substantially semi-cylindrical, with a length along a abutment longitudinal axis A1, abutment longitudinal axis A1 being substantially co-axial with that of post 20 and the anchor (not shown), a abutment juncture end 32 and a terminal end 34, abutment juncture end 32 and terminal end 34 being substantially normal to abutment longitudinal axis A1. Abutment juncture end 32 lies in a plane with post juncture end 24 of post 20 and has a lateral dimension greater than that of post juncture end 24, such that abutment 10 extends laterally beyond the perimeter of post 20. For purposes of disclosure, abutment 10 is depicted as being substantially semi-cylindrical, although it would be obvious to one skilled in the art that it could be of virtually any geometric shape without departing from the spirit of the present invention.

Abutment 10 deviates from the cylindrical as it rises from abutment juncture end 32 to terminal end 34, terminal end 34 forming only a segment of a circle. A radial segment 36 defines the semi-cylindrical portion of abutment 10, extending from abutment juncture end 32 to terminal end 34, substantially normal to both. A substantially rectalinear, sloping face 38 descends from a line proximate the longitudinal axis line A1 of the circle of terminal end 34 to the perimeter of abutment juncture end 32, opposite radial segment 36. A plurality of sloping faces 40 likewise slope from terminal end 34 to the perimeter of abutment juncture end 32, such that a tapering abutment 10, having an exterior shape which is anti-rotational within a waxing sleeve 50, detailed hereinbelow, is formed. It would be evident to one skilled in the art that the anti-rotational shape of abutment 10 could be of a variety of geometric shapes as long as the abutment 10 fits snugly within the waxing sleeve 50. An abutment exterior axis A2 is formed along the general center line of abutment 10 abutment exterior axis A2 substantially lying along a line defining a horizontal center of the infinite number of slices of the abutment along the length of the abutment.

Figure 5:
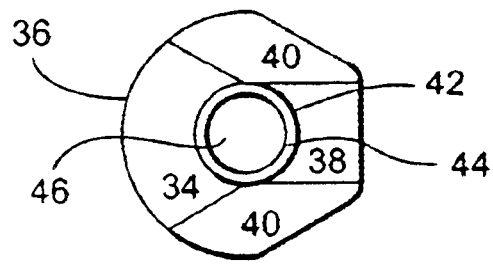
FIG. 5 is a top view of the abutment of the embodiment of FIG. 4.
Figure 4:
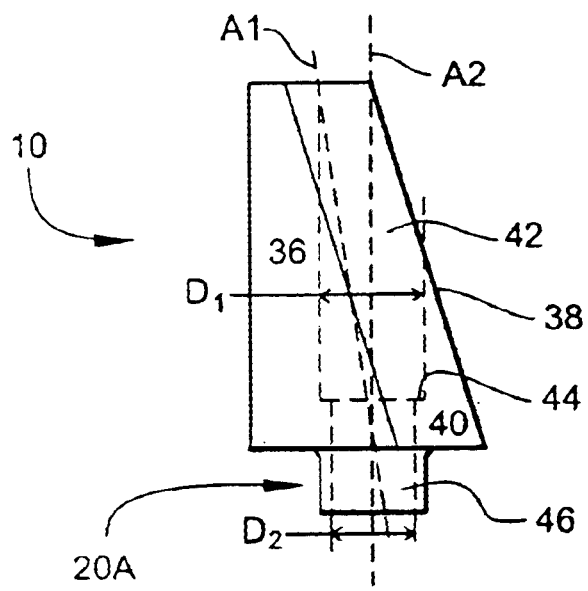
FIG. 4 is a side view of the abutment of the present invention in a screw attached embodiment lacking the post element.
Figure 6:
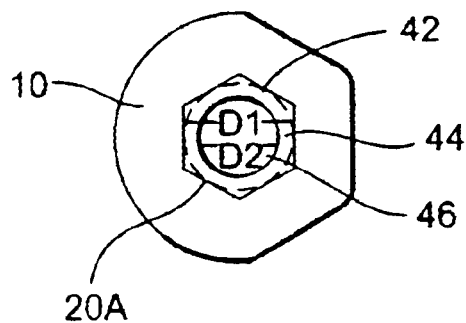
FIG. 6 is a bottom view of the abutment of FIG. 4.

Referring now to FIGS. 4 thru 6, the abutment 10 is presented in an embodiment wherein abutment 10 is attached to the anchor (not shown) by a screw (not shown) without the need for a full post, as in the first embodiment. Abutment 10 is formed as in the embodiment of FIGS. 1 thru 3, with two exceptions. Firstly, post 20 is replaced with a short base 20A which penetrates the cavity (not shown) of the anchor (not shown) only sufficiently to provide an anti-rotational relationship. Secondly, an internal bore 42 having a diameter D1 extends along abutment longitudinal axis A1 from terminal end 34, through the length of abutment 10 and base 20A. A step 44 is formed in internal bore 42 at a point along the length of internal bore 42 constricting internal bore 42 to a lesser diameter D2 at step 42. The diameter D1 of internal bore 44 is such that the head of an attachment screw 48 will fit within internal bore 42, but come to rest on step 44. The shank of a screw (not shown) passes through the smaller diameter D2, engaging the cavity (not shown) in the anchor (not shown).

Figure 7A:
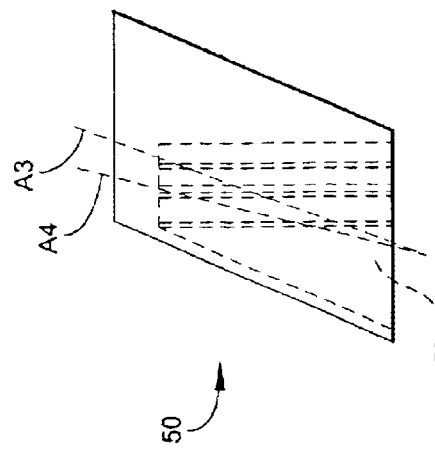
FIG. 7A is a side view of an alternate embodiment of the waxing sleeve of the present invention.
Figure 7:
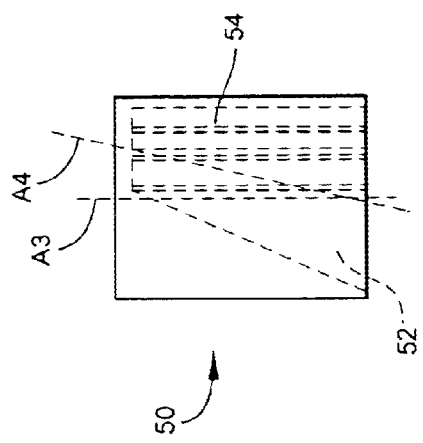
FIG. 7 is a side view of the waxing sleeve of the present invention.
Figure 8:
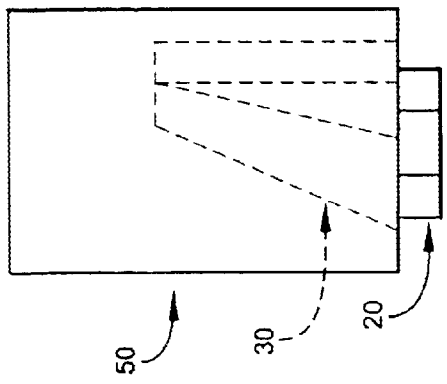
FIG. 8 is a side of the waxing sleeve in place on an abutment of the present invention.

Now referring to FIGS. 7 and 7A, waxing sleeve 50, formed of a polymer, has a substantially cylindrical exterior having axial and lateral dimensions nominally greater than those of abutment 10. Interior of waxing sleeve 50 is a cavity 52 conforming to the dimensions and shape of abutment 10 such that abutment 10 will fit snugly within waxing sleeve 50. A sleeve exterior axis A3 at FIG. 7 corresponds generally to longitudinal axis A1 of abutment 10 (FIGS. 1 and 4), while a sleeve exterior axis A3 at FIG. 7A departs from axis A1 of abutment 10 (FIGS. 1 and 4), while a sleeve interior axis A4 (FIGS. 7 and 7A) generally corresponds to abutment exterior axis A2 of abutment 10 (FIGS. 1 and 4).

Figure 7B:
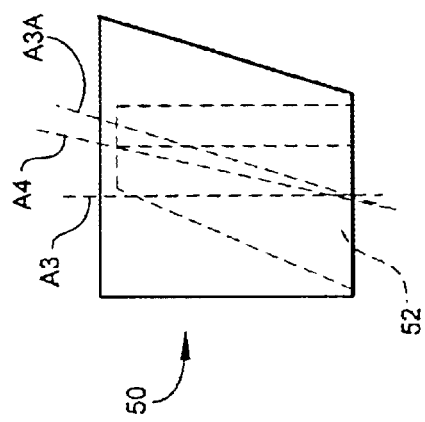
FIG. 7B is a side view of a second alternate embodiment of the waxing sleeve of the present invention.

In FIG. 7B, a second alternate embodiment in which the exterior of waxing sleeve departs from the cylindrical in at least one region of the perimeter thereof such that at least one pseudo sleeve exterior axis A3A is formed in addition to the sleeve exterior axis A3 of the cylinder. The combination of sleeve exterior axis A3 and pseudo sleeve exterior axis A3A allows a single waxing sleeve to be utilized in a multitude of different applications while requiring less build up of wax 56 to form a coping 60.

A plurality of relief grooves 54 may be formed in the walls of cavity 52, thereby providing gripping surfaces to which cement may adhere, and allowing excess cement to escape to the exterior of cavity 52 during the mating of the coping 50A (FIGS. 9 and 10) to the abutment 10.

Waxing sleeve 50 is adapted such that its external shape may be easily altered by carving or grinding away excess material. In an application in which a prosthesis is relatively aligned with the post, little material need be removed in the formation of the coping and a coping axis A5 (FIG. 9) may closely parallel axis A1 of abutment 10. In an application in which the prosthesis deviates from the longitudinal axial line A1 of abutment 10, material is removed from the waxing sleeve 50 and wax 56 added to the opposite side of waxing sleeve 50 such that a coping axis A5 (FIG. 10) may deviate greatly from axis A1. Coping axis A5 may vary greatly, being defined by the modifications made to waxing sleeve 50. In lieu of adding wax 56 to the waxing sleeve of FIG. 7, the waxing sleeve 50 of FIG. 7A or 7B may be used, thereby requiring the addition of less wax 56 (FIG. 10).

It would be evident to one skilled in the art that abutment 10 could be of a variety of different shapes without departing from the spirit of the present invention, and that waxing sleeve 50 could be adapted for cooperation with substantially any shape abutment 10, including many prior art cores.

The uniqueness of abutment 10 and waxing sleeve 50 of the present invention lies in the fact that the axial lines of the finished prosthesis relative to the anchor are so easily modified by the rotation of the abutment 10 in the anchor (not shown) and the modification of the waxing sleeve 50 by removing material from the waxing sleeve and/or adding wax 52 to the waxing sleeve 50, as illustrated in FIGS. 9 and 10.

Figure 11:
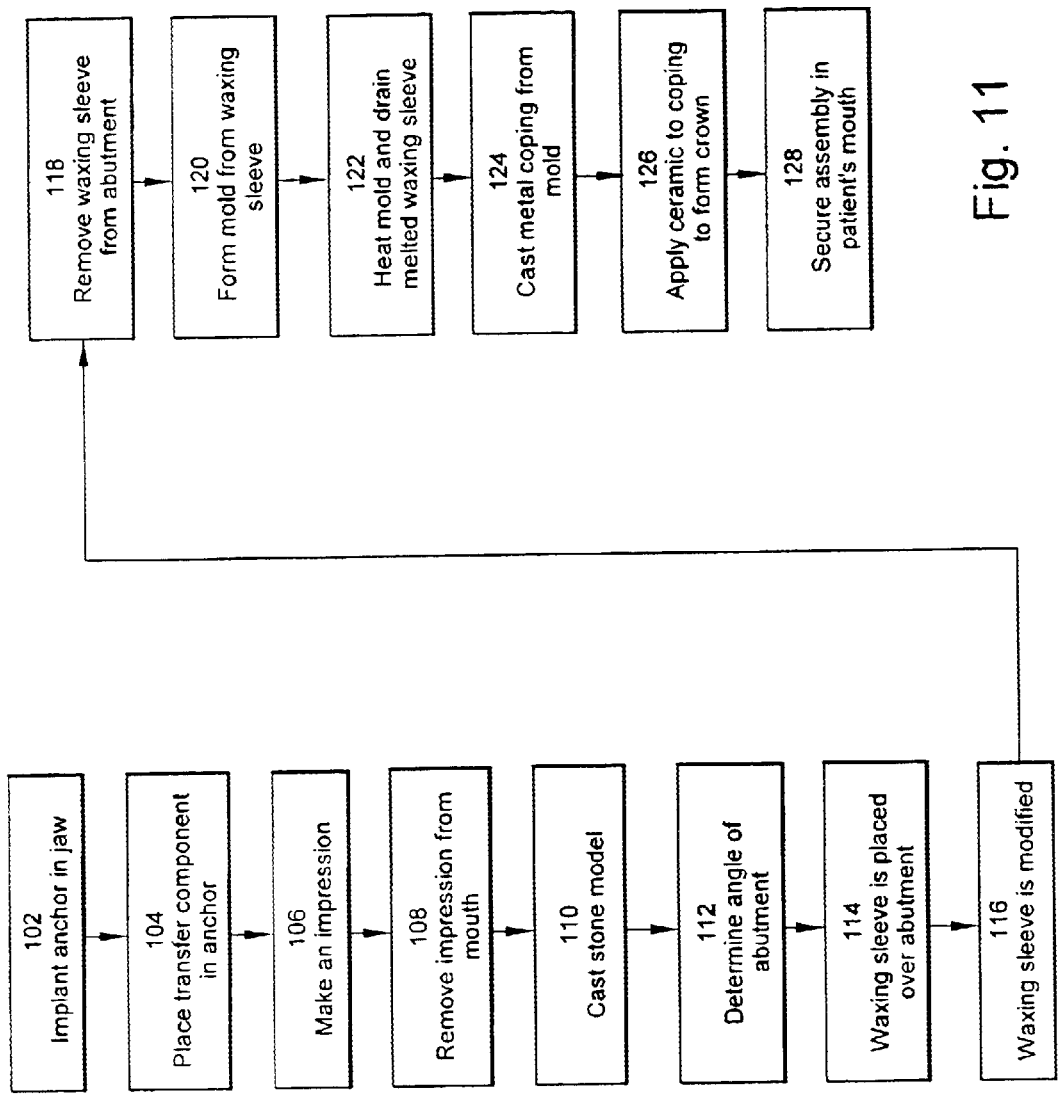
FIG. 11 is a flow chart of the procedures for the use of the abutment and waxing sleeve assembly of the present invention.

Procedures for the use of the post and core assembly 10 and waxing sleeve 50 is detailed hereinbelow and at FIG. 11.

102) An anchor is implanted into the jaw of a patient.

104) A transfer component (duplicate of post and core assembly 10), as is commonly known in the art, is temporarily placed into the anchor.

106) An impression is made of the patient's mouth, including the anchor, transfer component and surrounding teeth or prostheses, using any one of a variety of methods commonly known in the art.

108) The impression is removed from the patient's mouth and the transfer component is re-inserted into the impression, if it failed to separate from the anchor when the impression was removed.

110) An analog (duplicate of the implant anchor (not shown) is placed on the transfer component and a stone (plaster of paris) model is cast, using the impression as a mold.

112) The stone model is used to determine the angle at which the abutment must be placed, since the model is a duplicate of the patients mouth with the implant in it.

114) Waxing sleeve 50 is placed over the abutment 10.

116) The waxing sleeve 50 is trimmed (or added to with wax 50) until it is the desire shape of the coping (substructure of the prosthesis) that it will be cast into.

118) The waxing sleeve 50 is removed from the abutment 10.

120) A mold is formed from the waxing sleeve 50.

122) The mold is heated to melt and drain the waxing sleeve 50 from the interior thereof.

124) A metal coping is cast from the mold by any method as is commonly known in the art.

126) Ceramic 60 (FIGS. 9 and 10) is applied to the coping to form the crown, by a any method as is commonly known in the art.

128) The assembly is installed into the patient's mouth by securing the post 20 or base 20A into the anchor by means as are known in the art, and the crown is cemented to the abutment 10.

It is to be understood that the present invention is not limited to the embodiments described above, but encompasses any and all embodiments within the scope of the following claims.

What is claimed is:

1. A dental prosthesis abutment and waxing sleeve assembly comprising:
   an abutment, said abutment having:
      a longitudinal axis, and
      an abutment exterior axis, said abutment exterior axis substantially extending along a line defining a horizontal center of said abutment along the length of said abutment,
   the exterior of said abutment adapted to internally mate with
   a waxing sleeve, said waxing sleeve having:
      an internal cavity, said internal cavity being shaped and configured to conform to and matingly receive said abutment therein,
      a sleeve exterior axis, said sleeve exterior axis substantially extending along a line defining a horizontal center of the exterior of said waxing sleeve along the length of said waxing sleeve, and
      a sleeve interior axis, said sleeve interior axis substantially extending along a line defining a horizontal center along the length of said internal cavity of said waxing sleeve,
      said sleeve exterior axis differing from said sleeve interior axis,
   said waxing sleeve adapted to serve as a basis for forming a coping for a dental prosthesis.

2. A dental prosthesis abutment and waxing sleeve assembly, as defined in claim 1, wherein said abutment further comprises
   a post, said post adapted to mate with a prosthetic anchor implanted in the jaw of a patient, said post being of a shape generally corresponding to the shape of a cavity in the anchor.

3. A dental prosthesis abutment and waxing sleeve assembly, as defined in claim 2, wherein a first side of said abutment is substantially a cylindrical arc and a second side of said core is of an non-regular, anti-rotational shape, such that said waxing sleeve, when mated to said abutment, can not rotate around said abutment.

4. A dental prosthesis abutment and waxing sleeve assembly, as defined in claim 1, wherein said waxing sleeve further comprises a substantially cylindrical exterior surface.

5. A dental prosthesis abutment and waxing sleeve assembly, as defined in claim 4, wherein, when assembled,
   said abutment longitudinal axis is substantially co-axial with said sleeve exterior axis, said abutment exterior axis is substantially co-axial with said interior axis of said waxing sleeve, and said abutment exterior axis and said sleeve interior axis are oblique to said abutment longitudinal axis and said sleeve exterior axis.

6. A dental prosthesis abutment and waxing sleeve assembly, as defined in claim 4, wherein, when assembled, said sleeve exterior axis is oblique to said abutment longitudinal axis, said abutment exterior axis is substantially co-axial with said sleeve interior axis.

7. A dental prosthesis abutment and waxing sleeve assembly, as defined in claim 1, wherein a plurality of relief grooves are formed on an interior surface of said internal cavity of said waxing sleeve, said relief grooves being adapted to provide gripping surface for cementatious material and a route for excess cementatious material to escape from the interior of said internal cavity.

8. A dental prosthesis abutment and waxing sleeve assembly comprising:

an abutment, said abutment having:
a core having:
a longitudinal axis, and
an abutment exterior axis, said abutment exterior axis substantially extending along a line defining a horizontal center of said abutment along the length of said abutment, and
a base, said base adapted to mate with a prosthetic anchor implanted in the jaw of a patient, said base being of a shape generally corresponding to the shape of the anchor, the exterior of said abutment adapted to internally mate with a waxing sleeve, said waxing sleeve having:
an internal cavity, said internal cavity being shaped and configured to conform to and matingly receive said abutment therein,
a sleeve exterior axis, said sleeve exterior axis substantially extending along a line defining a horizontal center of the exterior of said waxing sleeve along the length of said waxing sleeve, and
a sleeve interior axis, said sleeve interior axis substantially extending along a line defining a horizontal center along the length of said internal cavity of said waxing sleeve,
said sleeve exterior axis differing from said sleeve interior axis, said waxing sleeve adapted to serve as a basis for forming a coping for a dental prosthesis.

9. A dental prosthesis abutment and waxing sleeve assembly, as defined in claim 8, wherein a first side of said abutment is substantially a cylindrical arc and a second side of said core is of an non-regular, anti-rotational shape, such that said waxing sleeve, when mated to said abutment, can not rotate around said abutment.

10. A dental prosthesis abutment and waxing sleeve assembly, as defined in claim 8, wherein said waxing sleeve further comprises a substantially cylindrical exterior surface.

11. A dental prosthesis abutment and waxing sleeve assembly, as defined in claim 10, wherein, when assembled, said abutment longitudinal axis is substantially co-axial with said sleeve exterior axis, said abutment exterior axis is substantially co-axial with said interior axis of said waxing sleeve, and said abutment exterior axis and said sleeve interior axis are oblique to said abutment longitudinal axis and said sleeve exterior axis.

12. A dental prosthesis abutment and waxing sleeve assembly, as defined in claim 10, wherein, when assembled, said sleeve exterior axis is oblique to said abutment longitudinal axis, and said abutment exterior axis is substantially co-axial with said sleeve interior axis.

13. A dental prosthesis abutment and waxing sleeve assembly, as defined in claim 8, wherein a plurality of relief grooves are formed on an interior surface of said internal cavity of said waxing sleeve, said relief grooves being adapted to provide gripping surface for cementatious material and a route for excess cementatious material to escape from the interior of said internal cavity.

14. A dental prosthesis abutment and waxing sleeve assembly comprising:

an abutment, said abutment having:
a core having:
a longitudinal axis, and
an abutment exterior axis, said abutment exterior axis substantially extending along a line defining a horizontal center of said abutment along the length of said abutment, the exterior of said abutment adapted to internally mate with a waxing sleeve, said waxing sleeve having:
an internal cavity, said internal cavity being shaped and configured to conform to and matingly receive said abutment therein,
at least one sleeve exterior axis, each of said sleeve exterior axes extending along a line generally defining a center along a length of a region around the perimeter of said waxing sleeve, and
a sleeve interior axis, said sleeve interior axis substantially extending along a line defining a horizontal center along the length of said internal cavity of said waxing sleeve,
at least one of said sleeve exterior axis differing from said sleeve interior axis, said waxing sleeve adapted to serve as a basis for forming a coping for a dental prosthesis.

15. A dental prosthesis abutment and waxing sleeve assembly, as defined in claim 14, wherein said waxing sleeve further comprises a substantially cylindrical exterior surface.

16. A dental prosthesis abutment and waxing sleeve assembly, as defined in claim 14, wherein, when assembled, each of said sleeve exterior axes is oblique to said abutment longitudinal axis, and said abutment exterior axis is substantially co-axial with said sleeve interior axis.

17. A dental prosthesis abutment and waxing sleeve assembly, as defined in claim 14, wherein a plurality of relief grooves are formed on an interior surface of said internal cavity of said waxing sleeve, said relief grooves being adapted to provide gripping surface for cementatious material and a route for excess cementatious material to escape from the interior of said internal cavity.

* * * * *